US005374236A

United States Patent [19]

Hassler

[11] Patent Number: 5,374,236

[45] Date of Patent: Dec. 20, 1994

[54] ELECTROMAGNETIC PRESSURE PULSE SOURCE

[75] Inventor: Dietrich Hassler, Uttenreuth, Germany

[73] Assignee: Siemens Aktiengesellschaft, Munich, Germany

[21] Appl. No.: 848,306

[22] Filed: Mar. 9, 1992

[30] Foreign Application Priority Data

Mar. 27, 1991 [DE] Germany ............................ 4110102

[51] Int. Cl.[5] ............................................ A61B 17/22

[52] U.S. Cl. ............................................ 601/2; 601/4; 128/660.03; 367/175

[58] Field of Search ........ 128/24 AA, 24 EL, 660.03, 128/660.01, 661.01; 606/128; 367/175

[56] References Cited

U.S. PATENT DOCUMENTS

| | | | |
|---|---|---|---|
| 4,757,820 | 7/1980 | Itoh | 128/24 AA |
| 4,901,709 | 2/1990 | Rattner | 128/24 EL |
| 4,928,672 | 5/1990 | Grasser et al. | 128/24 EL |
| 4,955,366 | 9/1990 | Uchiyama et al. | 128/24 EL |
| 4,972,826 | 11/1990 | Koehler et al. | 128/663.01 |
| 5,009,232 | 4/1991 | Hassler et al. | 128/24 EL |
| 5,025,789 | 6/1991 | Hassler | 128/24 EL |
| 5,058,569 | 10/1991 | Hassler et al. | 128/24 EL |
| 5,123,404 | 6/1992 | Takayama | 128/24 EL |
| 5,174,280 | 12/1992 | Gruenwald et al. | 128/24 EL |

FOREIGN PATENT DOCUMENTS

| | | | |
|---|---|---|---|
| 3739390 | 6/1989 | Germany | 128/660.03 |

*Primary Examiner*—Lee S. Cohen
*Assistant Examiner*—Brian L. Casler
*Attorney, Agent, or Firm*—Hill, Steadman & Simpson

[57] ABSTRACT

An electromagnetic pressure pulse source for generating focused pressure pulses as an electrically conductive membrane and a coil system which drives the membrane by rapidly displacing the membrane from the coil system. The coil system is formed by an annular array having a number of annular zones which can be individually activated to cause the generation of pressure pulses in variable chronological relation to each other, which permits the location of the focus of the resulting shockwave to be adjusted with a range, and/or the diameter of the focus to be changed.

34 Claims, 3 Drawing Sheets

ELECTROMAGNETIC PRESSURE PULSE SOURCE

BACKGROUND OF THE INVENTION

1. Field of the Invention

The present invention is directed to an electromagnetic pressure pulse source for generating focused pressure pulses, of the type having an electrically conductive membrane which is rapidly displaced by means of a coil system.

2. Description of the Prior Art

Electromagnetic pressure pulse sources having a membrane driven by a coil system as described, for example, in U.S. Pat. No. 4,674,505, are used for medical purposes in the treatment of calculosis, pathological bone conditions and pathological tissue changes. Such a pressure pulse source is normally applied to the body surface of the patient by means of a flexible coupling pillow, filled with a liquid medium for acoustic coupling. As a consequence of the flexibility of the coupling pillow, the spacing of the pressure pulse source from the body surface can be set, while maintaining contact between the coupling pillow and the body surface, so that the focus of the pressure pulses lies in the zone to be treated. The zone to be treated will be at a different depth below the surface dependent on the individual treatment case. Because the spacing of the focus from the body surface can be varied only to a slight extent in this manner, a number of proposals have been suggested to alleviate this situation. For pressure pulse sources wherein the pressure pulses are focused by an acoustic lens, for example, it is proposed in German OS 37 35 993 to provide two such acoustic lenses with variable spacing between the lenses to displace the focus, or alternatively to provide a lens having a variable focal length in the form of a liquid lens (vario lens).

All solutions heretofore proposed for displacing the focus have significant disadvantages associated therewith. In the aforementioned technique of displacing the focus by adjusting the distance of the pressure pulse source from the body surface of the patient, problems arise if the treatment zone lies immediately under the body surface, because of the small entry area for the pressure pulses which is then available. This results in the skin of the patient, which is sensitive to pain, experiencing high stress, such that hematoma can even occur. In the case of pressure pulse sources having an ultrasound B-scan applicator arranged in a central bore of the pressure pulse source for locating purposes, the B-scan applicator must be retracted if the zone to be treated lies close to the body surface, since it would otherwise be in the propagation path of the pressure pulses. This means that no ultrasound images, or only poor ultrasound images, can be produced while charging the patient with pressure pulses. Additionally, the necessary mechanism for adjusting the pressure pulse source, and possibly the B-scan applicator as well, involves considerable outlay.

The aforementioned pressure pulse source disclosed German OS 37 35 993 also has the above disadvantages, because although the mechanism for adjusting the pressure pulse source can be eliminated, a mechanism must nonetheless be provided for adjusting one of the lenses. This disadvantage can be avoided by using a vario lens for displacing the focus, however, a vario lens permits the focus to be displaced only slightly, and additionally involves a not inconsiderable design outlay and space requirement.

SUMMARY OF THE INVENTION

It is an object of the present invention to provide an electromagnetic pressure pulse source of the type having a coil system and electrically conductive membrane wherein the focus can be displaced over a broad range in a simple and economic manner.

It is another object of the present invention to provide such an electromagnetic pressure pulse source wherein the focus can be displaced without the use of complex mechanical means.

It is a further object of the present invention to provide such an electricmagnetic pressure pulse source wherein an ultrasound applicator can be contained in the pressure pulse source and can remain in contact with the surface of a subject while the subject is being irradiated by the pressure pulses (shockwaves).

Another object of the present invention is to provide such an electromagnetic pressure pulse source wherein the acoustic energy present in the region of the surface of the subject is substantially independent of the focal position which has been selected.

The above objects are achieved in accordance with the principles of the present invention in an electromagnetic pressure pulse source having focused pressure pulses which has an electrically conductive membrane and a coil system for driving the membrane by rapid displacement thereof, in which the coil system and membrane in combination form an annular array having a plurality of annular zones which can be individually activated to generate pressure pulses in variable chronological relationship to each other.

Background information relating to annular array technology in the context of ultrasound diagnostics is found in the article "Expanding-Aperture Annular Array," Dietz et al., Ultrasound Imaging, Vol. 1, No, 1, 1979, pages 56ff. The teachings of this article are incorporated herein by reference.

By fashioning the pressure pulse source as an annular array, it is possible to generate pressure pulses having differently curved wave fronts by suitable selection of the points in time at which the individual annular zones are activated, and respectively different positions of the focus of the pressure pulses can thus be set. This is undertaken in a purely electronic manner, so that all mechanical components are eliminated in conjunction with the displacement of the focus. The points in time at which the annular zones are to be activated to generate pressure pulses for achieving a defined focal position can be easily calculated from the average running times which arise between the individual annular zones and the focus which has been selected. If all annular zones are simultaneously activated to generate pressure pulses, the curvature of the wave front thus produced corresponds to that of the annular zones. In all other cases, the curvature of the wave front which is generated will deviate from that of the annular zones.

It is not necessary to change the physical spacing of the pressure pulse source relative to the surface of the subject to be sound-irradiated in order to displace the focus, so that the size of the surface of the subject which is to be charged with acoustic energy, and thus the stress experienced by that area, are essentially independent of the position of the focus which has been selected, which is particularly important in medical applications. Even when the zone to be acoustically irradiated, and thus the focus of the pressure pulses, lies immediately beneath the surface of the subject, a centrally arranged ultrasound B-scan applicator can be present and need not be retracted, so that a good image quality is always insured, and the mechanical components required for adjusting the position of the B-scan applicator can be eliminated.

For a defined position of the focus, the points in time at which the individual annular zones are activated to generate pressure pulses are normally selected under the assumption that the pressure pulses emanating from the individual annular zones will simultaneously arrive at the focus which has been selected. It is also possible, however, to enlarge the diameter of the focus so that the pressure present at the focus can be lowered by slight deviations of these points in time. The characteristic of the focus, i.e. the diameter thereof and the pressure occurring in the focus, can thus be adapted to individual applications. Moreover, any dependency of the pressure in the focus and/or the diameter of the focus on the focus position which has been selected can be compensated. Similarly, the aperture and/or the focus diameter as well as the pressure occurring in the focus can be influenced by suppressing activation for generating pressure pulses of the outermost or innermost annular zone.

In one embodiment of the invention, the coil system is arranged in a seating surface having sections allocated to the individual zones which are respectively fixed in space relative to each other. There is thus no change in the position of the zones relative to each other in order to displace the focus, or to vary its characteristic.

Annular array technology is also described in German OS 31 19 295 in the context of piezoelectric pressure pulse sources for generating focused pressure pulses. Such an annular array has not been achieved in practice, however, because of serious disadvantages. Known piezoelectric pressure pulse sources must have an extremely large diameter, in comparison to other types of pressure pulse sources, in order to achieve a defined pressure in the focus. This requires an extremely high number of annular zones, which in turn requires a significant technical outlay. Moreover, the outermost annular zones must be extremely narrow, which creates further technological problems because rings which are sufficiently narrow and which also have the required electrical strength are extremely difficult to manufacture. It has therefore been assumed by those of skill in the art that pressure pulse sources for generating focused pressure pulses cannot be practically achieved using an annular array technique, with justifiable outlay. This assumption is demonstrated in European application 0 327 917, wherein an attempt is made to retain the advantages of annular array technology while avoiding the disadvantages thereof. European Application 0 327 917 discloses a pressure pulse source having a plurality of individual transducers arranged in a mosaic pattern, wherein the individual transducers are mechanically adjusted for displacement of the focus, and can be driven with chronological offset.

The knowledge which those of skill in the art have relating to annular array techniques in piezoelectric technology cannot be automatically transferred to the context of an electromagnetic pressure pulse source since a person of skill in the art would assume that the portions of the coil system which would be allocated to the outer annular zones would have such a high inductivity that only a small current would flow when the coil system is charged with a high-voltage pulse in the standard manner for generating a pressure pulse. Because the pressure which can be achieved is approximately proportional to the square of the line density of the current flowing through the coil system, measured transversely relative to the winding direction, those of skill in the art would assume that electromagnetic pressure pulse sources making use of an annular array technique would have to have extremely large dimensions in order to achieve a defined pressure. This would mean that one of the important advantages of electromagnetic pressure pulse sources, namely their compact structure, would have to be sacrificed in order to make use of the annular array technique. The person of skill in the art would be additionally discouraged from pursuing the design of an electromagnetic pressure pulse source in an annular array technique because such a person would have assumed that the membrane would have to be formed by a plurality of separate membrane elements for each of the annular zones, which would require an enormous technological outlay.

It has been surprisingly shown, however, that the membrane in the preferred versions of the invention may be a common membrane for several annular zones, and in fact may be a common membrane for all annular zones, with the coil system for each of the annular zones being a separate coil arrangement. When a specific annular zone is activated to generate pressure pulses by charging the corresponding coil arrangement with a high-voltage pulse, the common membrane is not driven surface-wide (i.e., is not driven overall) as would be expected. To the contrary, a pressure wave which drives the membrane is only introduced into a localized region of the membrane situated in the immediate proximity of the coil arrangement which has been charged. The regions of the membrane associated with the annular zones which have not been activated to generate a pressure pulse remain essentially inactive. In order to further avoid against activated annular zones undesirably influencing inactivated annular zones, in an embodiment of the invention the common membrane is provided with annular expansion beads disposed between neighboring annular zones.

In a further embodiment of the invention, the annular zone and a generator for charging the coil arrangements respectively allocated to the annular zones with high-voltage pulses are dimensioned so that the pressure of the pressure pulses respectively emanating from the annular zones is substantially the same for each zone. This has a positive effect on the chronological course of the pressure pulse which results in the focus, because the pressure pulses emanating from the individual annular zones are substantially identically modified with respect to their pulse shape on their way to the focus as a result of non-linear compression properties of the media traversed by the pressure pulses. In a preferred embodiment, the coil arrangements for the respective annular zones are charged with high-voltage pulses of the same amplitude by the generator. A significant simplification of the generator is achieved as a result, because high-voltage pulses of the same amplitude are then required for all annular zones.

A reduction in the number of annular zones, and thus a reduction in the dimensions, particularly the diameter, of the pressure pulse source are achieved in an embodiment of the invention wherein the membrane and the coil arrangements in the respective regions of the annular zones are curved around a geometrical focus. Preferably the membrane and the coil arrangements are curved around a common geometrical focus in the region of an annular zone. As a result of this measure, the coil arrangements of even the outer annular zones have only slight inductivity, so that high currents flow in the coil arrangements as a consequence of high-voltage pulses of a given amplitude, and pressure pulses of a correspondingly high pressure can be produced. These advantages are particularly pronounced in a preferred embodiment wherein the membrane and the coil arrangements are spherically concavely curved in the region of each annular zone, and in particular have the same radius of curvature in the region of all annular zones. In this embodiment, both the coil arrangements and the membrane are arranged on a spherical cap. For annular zones it has been shown that a pressure pulse source of such a structure having a diameter of approximately 160 mm and a radius of curvature of the spherical cap of approximately 160 mm is sufficient to achieve a displacement of the focus amounting to a total range of 100 min. With a given high-voltage pulse amplitude supplied to the coil arrangements, the pressure achieved in the focus is independent of the position of the focus to an extent which is not significantly less than that of a conventional electromagnetic pressure pulse source having a spherical cap structure as disclosed, for example, in German OS 33 12 014.

A low number of annular zones is also achieved in a further version of the invention wherein the pressure pulse source is followed, in the direction of pulse propagation, by an acoustic lens, preferably a positive lens. The use of such a lens is advantageous with respect to the manufacturing outlay, because with such a lens the membrane and the coil system can be made planar. The acoustic lens is preferably a liquid lens, because such a lens can be constructed with a smaller thickness than solid lenses having the same focusing effect.

In other modifications of the invention, the pressure pulse source may have a reflector on which the generated pressure pulses are incident, the reflector being curved around a geometrical focus. A relatively low number of annular zones is required with this modification, because the reflector itself provides a certain focusing effect. A compact structure of the pressure pulse source is achieved if the annular zones emit pressure pulses in a substantial radial direction, and the reflector reflects the pressure pulses substantially in an axial direction. The reflector preferably annularly surrounds the pressure pulse source, because a large aperture can be thereby achieved.

In a preferred embodiment of the invention the outermost annular zone has an outside diameter in the range of 80 through 200 mm, and three through five annular zones are provided with a spherical curvature of the membrane and the coil arrangements. The membrane preferably has a radius of curvature which is also in a range between 80 and 200 mm, the radius of curvature preferably corresponding to the outside diameter of the outermost annular zone.

DESCRIPTION OF THE PREFERRED EMBODIMENTS

Figure 1:
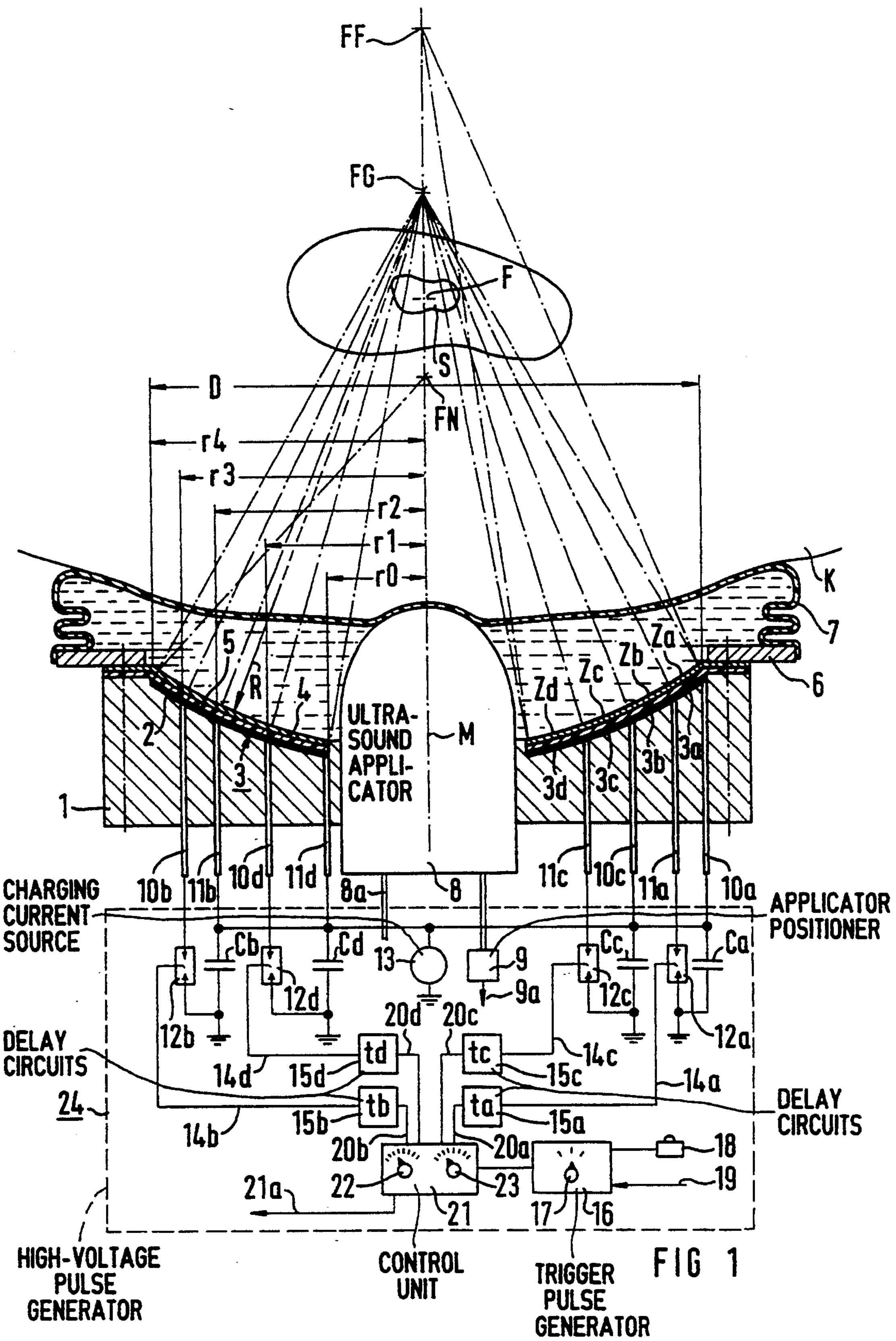
FIG. 1 shows a first embodiment of a pressure pulse generator constructed in accordance with the principles of the present invention in longitudinal section, with a block diagram showing the associated operating circuitry.

An electromagnetic pressure pulse source constructed in accordance with the principles of the present invention is shown in FIG. 1 in the form of a shockwave source for medical purposes. In the example of FIG. 1, the shockwave source is used for non-invasive disintegration of a kidney stone S in the body K of a patient. Although differing in the structure and operation of the membrane and coil arrangement, the overall structure of the shockwave source shown in FIG. 1 generally corresponds to the shockwave source disclosed in German OS 33 12 014. A coil carrier 1, consisting of electrically insulating material, has a seating surface 2 for a coil system generally referenced 3, which is spherically concavely curved around a geometrical focus FG of the shockwave source. A one-piece membrane 4, which is also spherically concavely curved around the geometrical focus FG, is disposed opposite that side of the coil system 3 facing away from the coil carrier 1. The membrane 4 consists of electrically conductive material, for example copper or aluminum. The coil system 3 and the membrane 4 are separated from each other by an insulating foil 5 of constant thickness. The membrane 4 is clamped at its peripheral edge between the coil carrier I and an annular retainer part 6 by means of screws, with only the center lines of two such screws being schematically indicated by dot-dash lines. A flexible coupling membrane 7, consisting of polymeric material, is attached to the retainer part 6. The space defined by the membrane 4, the retainer part 6 and the coupling membrane 7 is filled with a liquid, acoustic propagation medium, for example water, for the shockwaves emanating from the membrane 4.

In order to insure that the membrane 4, as shown, lies flush against the coil system 3 (with the insulating foil 5 interposed therebetween), measures not shown in FIG. 1 but disclosed in German OS 33 12 014 can be used which allow the water in the housing 6 to be placed under an elevated pressure in comparison to the ambient (atmospheric) pressure. Alternatively, the space between the membrane 4 and the coil system 3 can be evacuatable, as described in European Application 0 188 750.

The shockwave source has a central bore which extends through the coil carrier 1, the coil system 3, the insulating foil 5 and the membrane 4. An ultrasound head 8 of, for example, an ultrasound B-scan applicator, as part of an ultrasound locating system is received liquid-tight in this bore. The ultrasound head 8 is adjustable by a schematically indicated adjustment system 9, so as to be movable at least in the direction of the center axis M of the shockwave source, which proceeds through the geometrical focus FG. The ultrasound head 8 can thus be brought into contact with the body surface of the body K, with the coupling membrane 7 interposed therebetween, in the manner required for good image quality, as is shown in FIG. 1.

In contrast to the shockwave source disclosed German OS 33 12 014, the coil system 3 in the inventive embodiment of FIG. 1 is not formed by a single, spherically curved coil having helically turns arranged on the seating surface 2. Instead, the coil system 3 is formed by four annular coils 3*a*, 3*b*, 3*c* and 3*d* arranged concentrically relative to the center axis M of the shockwave source. These annular coils have respective terminals 10*a* through 10*d* and 11*a* through 11*d*. The turns of the annular coils 3*a* through 3*d* respectively connecting the associated terminal pairs are helically wound on the seating surface 2. The annular coils 3*a* through 3*d* are connected via the terminals 10*a* through 10*d* and 11*a* through 11*d* to a high-voltage pulse generator 24, schematically shown in a block diagram. The pulse generator 24 includes respective high-voltage capacitors Ca through Cd for each of the annular coils 3*a* through 3*d*. Each annular coil 3*a* through 3*d* also has a triggerable spark gap 12*a* through 12*d* allocated thereto. The spark gaps 12*a* through 12*d* permit the respective high-voltage capacitors Ca through Cd to be discharged into the respective annular coils 3*a* through 3*d* . The high-voltage capacitors Ca through Cd are connected to a single charging current source 13 with which the high-voltage capacitors Ca through Cd can be charged to a high-voltage, for example 20 kV. The trigger electrodes of the spark gaps 12*a* through 12*d* are connected to the output of a trigger pulse generator 16 via respective trigger lines 14*a* through 14*d* which contain respective pulse delay circuits 15*a* through 15*d*. The trigger pulse generator 16 has a switch 17 and, depending on the position of the switch 17, provides either an internally generated periodic sequence of trigger pulses having a frequency of, for example, 2 Hz, or a single trigger pulse upon the actuation of a key 18 connected to the trigger pulse generator 16, or a single trigger pulse when a control pulse is supplied to the trigger pulse generator 16 via a line 19. The control pulse on the line 19 may be derived in a known manner from a periodic body function of the patient, for example from the respiratory cycle.

The delay times ta through td of the respective pulse delay circuits 15*a* through 15*d* can be set via respective control lines 20*a* through 20*d*. The control lines 20*a* through 20*d* are connected to a control unit 21 having two adjustment knobs 22 and 23. The adjustment knob 22 serves the purpose of displacing the acoustic focus between the positions FN and FF along the center axis M of the shockwave source, the position FN being located closer to the shockwave source than the geometrical focus FG and the position FF being farther from the shockwave source than the geometrical focus FG. The adjustment knob 23 serves the purpose of varying the diameter of the acoustic focus. As used herein, the term "acoustic focus" is that region surrounding the location of maximum pressure which is limited by the −6dB isobar. The acoustic focus is therefore that region wherein the pressure is at least half the maximum occurring pressure. As used herein, the diameter of the acoustic focus means the maximum diameter thereof in a plane proceeding at a right angle relative to the center axis M of the shockwave source.

When one of the spark gaps 12*a* through 12*d* is triggered, the corresponding high-voltage capacitor Ca through Cd discharges rapidly into the corresponding annular coil 3*a* through 3*d* . The pulse-like current which is thereby caused to flow through the respective annular coil 3*a* through 3*d* has an associated magnetic field. As a consequence of this magnetic field, eddy currents are induced in that annular region of the membrane 4 disposed opposite the energized coil 3. The direction of the eddy currents in the annular region of the membrane is opposite to the direction of the current flowing in the energized annular coil. The eddy currents thus have an associated magnetic field which is oppositely directed to the magnetic field associated with the current flowing in the energized coil. Repelling forces are thereby generated between the energized coil and the associated annular region of the membrane 4, which cause a pressure pulse to be initiated into the water adjacent the annular region of the membrane 4. This pressure pulse is in the form of an annular wave front which is spherically curved, substantially around the geometrical focus FG. The pressure pulse intensifies in its propagation path through the water and through the body tissue of the patient to gradually form a shockwave. As used herein, a "shockwave" means a pressure pulse having an extremely steep rising (leading) edge. The term "shockwave" will always be used for simplicity, regardless of whether a generated pressure pulse has already intensified to form a shockwave. The shockwave source of FIG. 1 thus has four annular zones Za through Zd which can be activated to independently generate shockwaves relative to each other. For the geometrical focus FG, the margin rays of the pressure pulses of the respective annular zones Za through Zd are indicated with dot-dash lines. The sections of the seating surface which carry the annular coils 3*a* through 3*d* associated with the zones Za through Zd are stationary relative to each other.

The control unit 21 is constructed so that the delay times ta through td are of identical size when the adjustment knob 22 is, for example, in a middle setting position. When the adjustment knob 22 is brought to this position and a trigger pulse from the trigger pulse generator 16 is supplied to the pulse delay circuits 15*a* through 15*d* , the annular zones Za through Zd are thus simultaneously activated to generate shockwaves. As a consequence of the spherical curvature of the membrane 4 and of the annular coils 3*a* through 3*d* , the resulting shockwaves simultaneously arrive in the acoustic focus forming in the immediate proximity of the geometrical focus FG, having the effect of a single shockwave being formed at that location. The control unit 21 is further fashioned so that when the adjustment knob 22 is set at one extreme position, the delay times ta through td are set so that a trigger pulse for activating the outermost annular zone Za occurs first, followed by triggering of pulses in the annular zones Zb and Zd, Zc and the innermost annular zone Zd. The delay times ta through td are matched to each other so that the respective shockwaves emanating from the individual annular zones Za through Zd simultaneously arrive in the position FN of the acoustic focus. When the adjustment knob 22 is set at the opposite extreme setting position, the delay times ta through td are set so that the innermost annular zone Zd is first triggered and is thus first activated to generate a shockwave, followed by the zones Zc, Zb and the outermost zone Za. Again, the delay times ta through td are selected so that the shockwaves emanating from the respective annular zones Za through Zd simultaneously arrive in the position FF of the acoustic focus. Between these two extreme positions of the adjustment knob 22, the delay times ta through td are varied so that the acoustic focus can be shifted between the extreme positions FN and FF with infinite variation, the above-explained special case arising when all delay times ta through td are identical. The delay times ta through td are set for each position of the acoustic focus so that, as stated above, the respective shockwaves emanating from the individual annular zones Za through Zd simultaneously arrive in the acoustic focus which has been selected.

The individual pulses arrive simultaneously at the selected focus location, however, only when the adjustment knob 23 is set at one extreme position. The control unit 21 is constructed so that, as the adjustment knob 23 is adjusted in the direction of its other extreme position, the delay times ta through td increasingly deviate from those delay times for which the shockwaves emanating from the annular zones Za through Zd would simultaneously arrive at the selected acoustic focus. The maximum deviation in the case of the described exemplary embodiment is to ±100% of the delay times ta through td required for the simultaneous arrival of the shockwaves at the selected acoustic focus. Once a location for the acoustic focus has been selected, a maximum pressure and a smallest focus diameter will result in the case of the simultaneous arrival of all shockwaves at the selected acoustic focus. With increasing deviation of the delay times ta through td, the maximum pressure is increasingly reduced and the diameter of the acoustic focus is increasingly enlarged from the case which would occur with identical delay times. This permits the maximum pressure and the acoustic focus diameter to be adapted to individual requirements. For deviations in the delay times ta through td by ±100%, a reduction in the maximum pressure by approximately 50% occurs, and an enlargement in the diameter of the acoustic focus by approximately 100% occurs. In the exemplary embodiment described in FIG. 1, the control unit 21 is constructed so that, given positions of the adjustment knob 23 deviating from the extreme position causing simultaneous arrival of the shockwaves, the delay times ta and tc are varied so that the shockwaves emanating from the annular zones Za and Zc simultaneously arrive at a point which is at a greater distance from the shockwave source than the acoustic focus set by means of the adjustment knob 22 alone. The delay times tb and td are set by the control unit 21 so that the shockwaves emanating from the annular zones Zb and Zd simultaneously arrive at a point which is closer to the shockwave source than the acoustic focus which has been set by the adjustment knob 22 alone. The extent to which these points lie outside the acoustic focus in one or the other direction increases as the position of the adjustment knob 23 increasing deviates from the one extreme position causing simultaneous arrival.

As can be seen in FIG. 1, the outermost and innermost boundary rays of the pressure pulses for the cases of focusing onto FN and FF are shown in dot and dash lines, from which is apparent that displacement of the focus has substantially no influence on the size of the area of the body surface of the patient charged with acoustic energy. Thus pain or hematoma will not occur even if stones lying immediately under the body surface are treated. As can also be seen in FIG. 1, the ultrasound head 8 can remain in engagement with the surface of the body K (with the coupling membrane 7 interposed therebetween) even given the shortest possible focal distance FN, without the ultrasound head 8 being situated in the propagation path of the shockwaves.

The annular zones Za through Zd, and the corresponding annular coils 3*a* through 3*d*, are dimensioned so that, taking the capacitances and the charging voltages of the capacitors Ca through Cd into consideration (both the charging voltages and the capacitances are identical for each zone in the case of the exemplary embodiment), the shockwaves each achieve the same pressure in the unfocused condition, i.e., in the immediate proximity of the membrane 4. This is the case in the pressure pulse source shown in FIG. 1, for example, when the outside diameter D of the outermost annular zone Za and the radius of curvature R of the membrane 4 each amount to 160 mm, the radii r0 through r4 are respectively 30 mm, 45 mm, 61 mm, 63 mm and 80 mm, and the annular coils 3*a* through 3*d* are respectively formed by eight turns of a I mm diameter wire, 9 turns of a 1.5 mm diameter wire, 12 turns of a 1.5 mm diameter wire, and 14 turns of a 1 mm diameter wire.

Given such dimensioning, the resulting inductances of the annular coils 3*a* through 3*d* are on the order of magnitude of a few $\mu$H, as in the case of conventional pressure pulse sources. This means that, given an overall capacitance of the high-voltage capacitors Ca through Cd corresponding to the capacitance which is standard in conventional practice, currents having approximately the same amplitude as in conventional pressure pulse sources will flow in the coils. The different wire diameters are not shown in FIG. 1, and the wire diameter of the annular coils 3*a* through 3*d* as well as the thicknesses of the membrane 4 and the insulating foil 5 are shown exaggerated for clarity. With the aforementioned dimensioning, the focus of the shockwaves can be displaced by a total of 100 mm without producing a noteworthy loss in pressure. The focus position FN having the smallest distance from the shockwave source has a distance of approximately 54 mm from the geometrical focus FG.

One terminal of each of the high-voltage capacitors Ca through Cd is at grounded potential. The high-voltage capacitors Ca through Cd are connected via coaxial lines (not shown in FIG. 1) to the annular coils 3*a* through 3*d* (as well as via the respective spark gaps 12*a* through 12*d* ) so that a high difference in potential occurs only between the annular coils 3*b* and 3*c*. Increased insulation must therefore only be provided between the annular coils 3*b* and 3*c*, as indicated in FIG. 1 by the somewhat larger spacing between these coils. The spaces between the annular coils 3*d* as well as between their respective turns, moreover, are filled with an insulating casting resin in a known manner, but not shown in the drawings.

For conducting treatment, the shockwave source and the body K of the patient are first positioned relative to each other so that the calculus to be disintegrated is located on the center axis M of the shockwave source. This occurs using the ultrasound locating system to which the ultrasound head 8 is connected via a line 8*a*. A line-shaped mark is mixed into the ultrasound image displayed on a picture screen (not shown) in a known manner, the position of the mark corresponding to that of the center axis M. Subsequently, the acoustic focus is displaced by actuating the adjustment knob 22 so that it coincides with the mark, as indicated in FIG. 1 by the designation for the acoustic focus F. The position of the acoustic focus can be checked in the ultrasound image with reference to a mark whose position changes upon actuation of the adjustment knob 22 in accord with the displacement of the acoustic focus. Corresponding data are supplied to the ultrasound locating system by the control unit 21 via a line 21*a*. Because the position of the mark identifying the acoustic focus is dependent on the position of the ultrasound head along the center axis M, data identifying the position of the ultrasound head on the center axis M are supplied to the ultrasound locating system from the adjustment unit 9 via a line 9*a*. When the acoustic focus has been set in the described manner, the stone S is disintegrated into fragments with a series of shockwaves, until the fragments are so small that they can be eliminated naturally.

Figure 2:
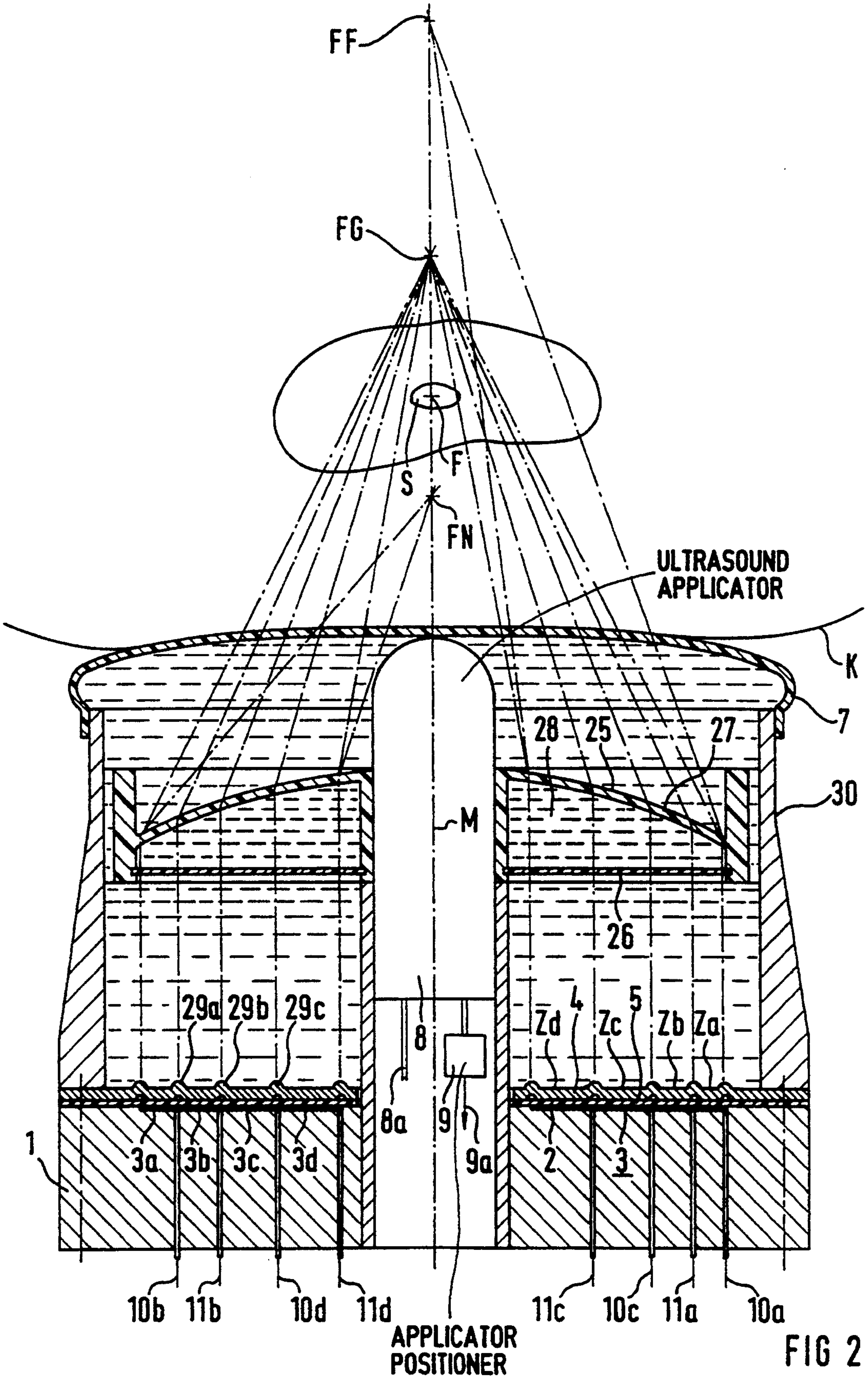
FIG. 2 shows a second embodiment of a pressure pulse generator constructed in accordance with the principles of the present invention in longitudinal section.

A further embodiment of a shockwave source constructed in accordance with the principles of the present invention is shown in FIG. 2 wherein elements identical or similar to those already discussed in connection with FIG. 1 are provided with the same reference symbols. The primary difference between the embodiments of FIG. 1 and FIG. 2 is that the embodiment of FIG. 2 has a seating surface 2 which is planar, disposed at one end of a tubular housing 30 to which the coil carrier 1 is attached by screws or suitable fasteners indicated with dot-dash lines. Consequently, the coil system formed by the annular coils 3*a* through 3*d* , the membrane 4 and the insulating foil 5 are also planar. As a substitute for the lack of the spherical curvature, the shockwave source of FIG. 2 has an acoustic positive lens in the form of a plano-convex liquid lens 25 disposed in the path of shockwave propagation toward the subject. The liquid lens has an entry wall 26 consisting of polymethyipentene (TPX), an exit wall 27 consisting of polytetrafluorethylene, and contains a lens liquid 28 enclosed between the entry wall 26 and exit wall 27. The lens liquid 28 is a fluorocarbon liquid, for example Flutec PP3® or Fluorinert FC75®.

Because the housing 30, closed at its opposite end by the coupling membrane 7, contains water as the propagation medium for the shockwaves, and the speed of sound is lower in the lens fluid 28 than in water, the plano-convex shape of the liquid lens 25 effects a focusing of the shockwaves onto the geometrical focus FG which lies on the center axis M of the shockwave source, when the annular zones Za through Zd are simultaneously activated to generate a pressure pulse. Due to the simultaneous activation of the annular zones Za through Zd, a single planar shockwave arrives at the liquid lens 25. By actuating the adjustment knobs 22 and/or 23 of the high-voltage pulse generator 24 (not shown again in FIG. 2) in the manner described above in connection with the embodiment of FIG. 1, the focus of the shockwaves can be shifted with infinite variation between the positions FN and FF, or a variation in the pressure and the diameter of the acoustic focus can be effected.

The liquid lens 25 may alternatively be of a biconvex shape. The use of the liquid lens 25 offers the advantage of lower thickness in comparison to a plano-concave or biconcave solid lens which would, for example, consist of polystryol. The use of a liquid lens 25, however, can introduce non-linearities in the event of transmission at extremely large acoustic powers, because of the highly non-linear compression properties of the lens fluid 28.

In the embodiment of FIG. 2, the membrane 4 includes expansion beads 29*a* through 29*c* disposed between the annular zones Za through Zd which increase the elasticity of the membrane 4 and thus prevent a premature failure due to elevated mechanical stresses. As shown in FIG. 2, further expansion beads can be provided at the outer edge of the annular zone Za and at the inner edge of the annular zone Zd.

Figure 3:
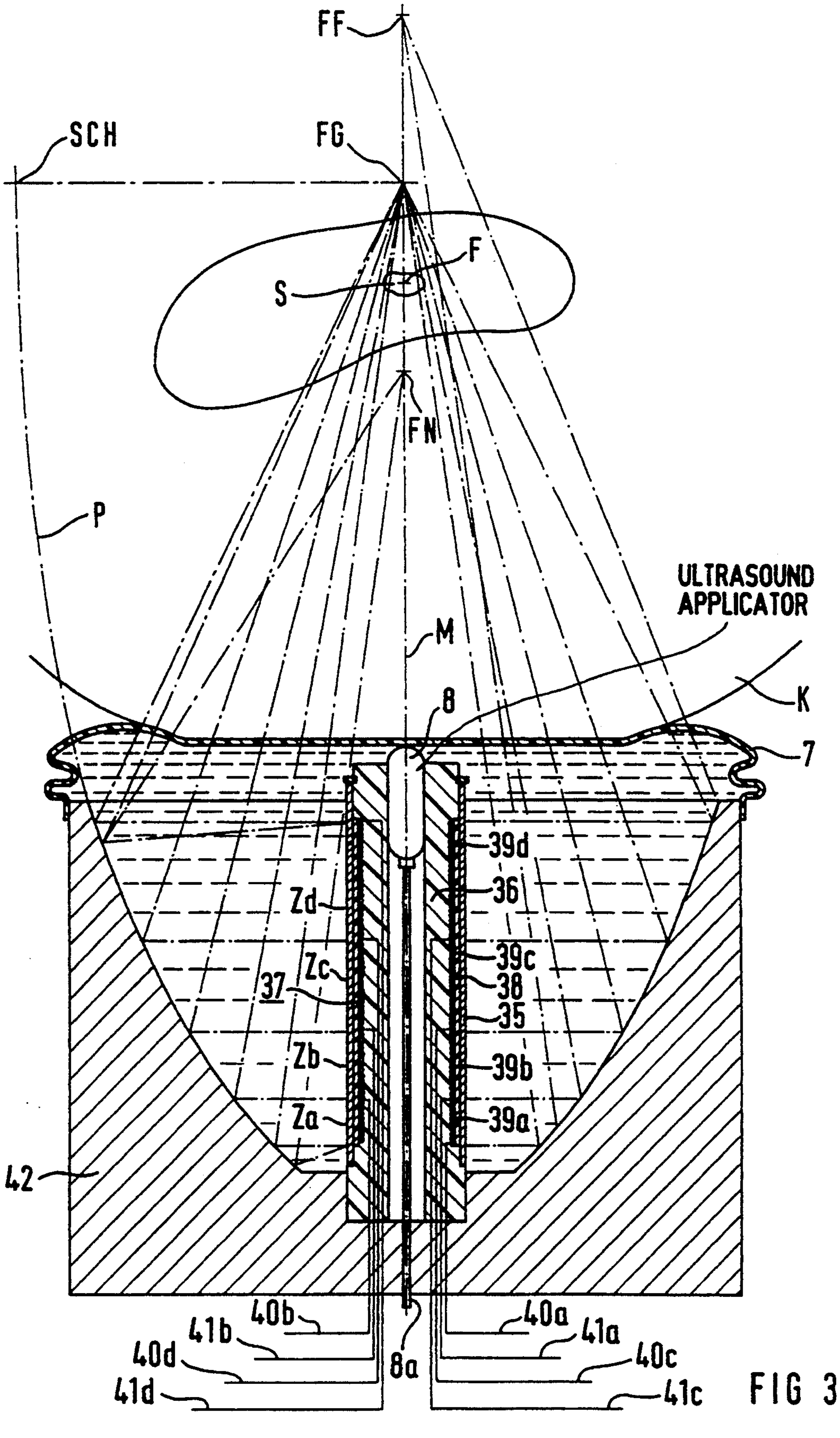
FIG. 3 shows a third embodiment of a pressure pulse generator constructed in accordance with the principles of the present invention in longitudinal section.

The pressure pulse source shown in the embodiment of FIG. 3 is constructed according to the principles of a LARS source (large aperture ring-shaped sound source) as generally described in German OS 38 35 318. In this embodiment, a radially outwardly emitting, tubular membrane 35 is used as the displaceable membrane, which is driven by a coil system 37 disposed inside the membrane 35 and wound helically around a tubular coil carrier 36. The membrane 35 and the coil system 37 are separated from each other by an insulating foil 38. The coil system 37 is subdivided into four tubular coils 39*a* through 39*d* disposed in axial succession on the coil carrier 36. The coils 39*a* through 39*d* are connected to a high-voltage pulse generator 24 (as shown in FIG. 1, but not shown in FIG. 3) via terminals 40*a* through 40*d* and 41*a* through 41*d* in a manner analogous to that shown in FIG. 1.

When the tubular coils 39*a* through 39*d* are charged, the respective regions of the membrane 35 surrounding the charged coil expands, resulting in the introduction of a shockwave into the water contained in the shockwave generator as a propagation medium. A total of four annular zones Za through Zd are thus present, which can be activated to emit radially propagating shockwaves. The shockwaves are incident on a reflector 42 annularly surrounding the membrane 35, having a reflector face produced by the rotation of a section of a parabola P, indicated with dot-dashed lines, and having a focal point coinciding with the geometrical focus FG of the arrangement, which lies on the center axis M of the shockwave source. The vertex SCH of the parabola P lies on a straight line which intersects the center axis M at a right angle. When all four annular zones Za through Zd are simultaneously activated to generate a shockwave, a shockwave having a cylindrical wave front is introduced into the water, which is then focused by the reflector 42 onto the focal point of the parabola P. By actuating the adjustment knobs 22 and 23 of the high-voltage pulse generator 21, the acoustic focus can be displaced between the positions FF and FN, or the pressure and the diameter of the acoustic focus can be varied, as described above.

The ultrasound head 8 is arranged in a central bore of the coil carrier 36 so as to be longitudinally displaceable therein. The ultrasound head 8 has associated adjustment elements as described above in connection with FIG. 1, but which are not shown in FIG. 3.

All of the above exemplary embodiments have in common the advantage that adjustability of the acoustic focus is achieved over a broad range, for example, of 100 mm, and to achieve this result the shockwave source constructed as an annular array need only have four annular zones. The additional outlay over conventional shockwave sources is maintained within reasonable limits because a common membrane can be employed for all annular zones. It is only necessary to undertake a subdivision of the coil system into a plurality of annular or tubular coils corresponding in number to the plurality of annular zones, to provide a plurality of smaller capacitors corresponding in number to the plurality of annular zones instead of a large capacitor, and to provide a plurality of spark gaps corresponding in number to the plurality of annular zones instead of one spark gap. Relatively uncomplicated electronics in the form of the above-described control unit and pulse delay circuits can be used. For applications wherein a reduction in the quality of the focusing and/or of the adjustment range of the acoustic focus are acceptable, three annular zones may be adequate.

In each of the above embodiments, physical focusing of the shockwaves is employed, by means of the spherical curvature in the embodiment of FIG. 1, the acoustic lens in the embodiment of FIG. 2, and the curvature of the reflector in the embodiment of FIG. 3. It is still within the inventive concept disclosed herein, however, to undertake focusing exclusively by electronic means, however, this would require an increased number of annular zones to obtain the same acoustic focus adjustability and the same quality of the focus as are achieved in the embodiments specifically shown in FIGS. 1, 2 and 3.

The above exemplary embodiments have been set forth in the context of a pressure pulse source for the disintegration of calculi. It will be understood by those of skill in the art, however, that the principles and structure disclosed herein can be used for other medical purposes as well as for non-medical purposes.

Although modifications and changes may be suggested by those skilled in the art, it is the intention of the inventor to embody within the patent warranted hereon all changes and modifications as reasonably and properly come within the scope of his contribution to the art.

I claim as my invention:

1. An electromagnetic pressure pulse source comprising:

a housing containing an acoustic propagation medium;

electrically conductive membrane means disposed for interacting with said propagation medium and coil means, forming in combination an annular array having a plurality of annular zones, for generating pressure pulses in said acoustic propagation medium, said pressure pulses converging at a common acoustic focus having a position and size; and means for energizing said coil means for respectively rapidly displacing said membrane means in said annular zones relative to said acoustic propagation medium in variable chronological relationship for selectively adjusting at least one of the position or size of said acoustic focus.

2. An electromagnetic pressure pulse source as claimed in claim 1, further comprising a carrier for said coil means having a seating surface on which said coil means are disposed, said seating surface having a plurality of sections respectively allocated to said annular zones, said sections being stationary relative to each other.

3. An electromagnetic pressure pulse source as claimed in claim 1 wherein said membrane means comprises a single, common membrane for a portion of said plurality of annular zones, and wherein said coil means comprises a plurality of separate coil arrangements respectively associated with each of said annular zones.

4. An electromagnetic pressure pulse source as claimed in claim 3 wherein said membrane means comprises a single, common membrane for all of said annular zones.

5. An electromagnetic pressure pulse source as claimed in claim 3 wherein said common membrane has at least one annular expansion bead disposed between at least two of said annular zones which neighbor each other.

6. An electromagnetic pressure pulse source as claimed in claim 1 wherein said annular zones and said means for energizing said coil means are dimensioned so that said pressure pulses respectively emanating from said annular zones are substantially the same pressure.

7. An electromagnetic pressure pulse source as claimed in claim 1 wherein said coil means includes a plurality of coil arrangements respectively associated with said annular zones, and wherein said means for energizing said coil means comprises means for charging said respective coil arrangements with high-voltage pulses of the same amplitude.

8. An electromagnetic pressure pulse source as claimed in claim 1 wherein each annular zone has a respective geometrical focus associated therewith, and wherein said membrane means and said coil means, in a region of each annular zone, are curved around the geometrical focus associated with that annular zone.

9. An electromagnetic pressure pulse source as claimed in claim 8 wherein said membrane means and said coil means are spherically concavely curved in the region of each annular zone.

10. An electromagnetic pressure pulse source as claimed in claim 8 wherein said membrane means and said coil means have the same radius of curvature in the region of all of said annular zones.

11. An electromagnetic pressure pulse source as claimed in claim 1 wherein all of said annular zones have a common geometrical focus, and wherein said membrane means and said coil means are curved around said common geometrical focus in a region of all of said annular zones.

12. An electromagnetic pressure pulse source as claimed in claim 11 wherein said membrane means and said coil means are spherically concavely curved around said common geometrical focus in the region of all of said annular zones.

13. An electromagnetic pressure pulse source as claimed in claim 1 wherein said membrane means and said coil means have the same radius of curvature in a region of all of said annular zones.

14. An electromagnetic pressure pulse source as claimed in claim 1 further comprising an acoustic lens disposed in the propagation path of said pressure pulses for focusing said pressure pulses onto a geometrical focus.

15. An electromagnetic pressure pulse source as claimed in claim 14 wherein said acoustic lens is a positive lens.

16. An electromagnetic pressure pulse source as claimed in claim 14 wherein said acoustic lens is a liquid lens.

17. An electromagnetic pressure pulse source as claimed in claim 1 further comprising reflector means disposed in the propagation path of said pressure pulses for focusing said pressure pulses onto a geometrical focus.

18. An electromagnetic pressure pulse source as claimed in claim 17 wherein said reflector means is a surface curved around said geometrical focus.

19. An electromagnetic pressure pulse source as claimed in claim 17 wherein said annular zones are disposed for emitting said pressure pulses in a substantially radial direction relative to said housing and wherein said reflector means is a means for reflecting the substantially radially emitted pressure pulses in a substantially axial direction relative to said housing.

20. An electromagnetic pressure pulse source as claimed in claim 17 wherein said reflector means annularly surrounds said coil means and said membrane means.

21. An electromagnetic pressure pulse source as claimed in claim 1 wherein said plurality of annular zones includes at least three annular zones, one of which is an outermost annular zone, and wherein said outermost annular zone has an outside diameter in the range of 80 through 200 min.

22. An electromagnetic pressure pulse source as claimed in claim 19 wherein said membrane means is curved and has a radius of curvature in the range of 80 through 200 mm.

23. An electromagnetic pressure pulse source as claimed in claim 1 further comprising means for locating a selected structure within a subject irradiated by said pressure pulses including means for generating a locating field disposed in said housing out of the propagation path of said pressure pulses.

24. An electromagnetic pressure pulse source as claimed in claim 23 wherein said means for generating a locating field is an ultrasound applicator.

25. An electromagnetic pressure pulse source as claimed in claim 1 further comprising locating means for identifying a selected structure within a subject to be irradiated by said pressure pulse sources, said locating means including applicator means for generating a locating field, and said coil means and said membrane means having respective central openings through which said locator means extends into said propagation medium.

26. An electromagnetic pressure pulse source comprising:

a housing containing an acoustic propagation medium;

a plurality of individually energizable annular coils;

an electrically conductive common membrane disposed between said coils and said propagation medium for interacting with said propagation medium for generating pressure pulses in said propagation medium, said pressure pulses converging at a common acoustic focus having a position and size, and said annular membrane having a plurality of annular zones respectively in registry with said coils; and means for selectively individually energizing said coils for respectively rapidly displacing said membrane in said annular zones relative to said acoustic propagation medium in variable chronological relationship for selectively adjusting at least one of the position or size of said acoustic focus.

27. An electromagnetic pressure pulse source as claimed in claim 26 wherein said coils and said common membrane are curved around a geometrical focus.

28. An electromagnetic pressure pulse source as claimed in claim 26 wherein said coils and said common membrane are planar.

29. An electromagnetic pressure pulse source as claimed in claim 28 further comprising means for focusing said pressure pulses onto a geometrical focus.

30. An electromagnetic pressure pulse source as claimed in claim 26 wherein said coils and said membrane are cylindrical.

31. An electromagnetic pressure pulse source as claimed in claim 30 further comprising an acoustically reflective surface disposed surrounding said cylindrical coils and membrane for reflecting said pressure pulses onto said geometrical focus.

32. An electromagnetic pressure pulse source comprising:

a housing containing an acoustic propagation medium;

a carrier disposed in said housing having a surface curved around a geometrical focus;

electrically conductive membrane means disposed for interacting with said propagation medium and coil means, forming in combination an annular array having a plurality of annular zones disposed on said surface of said carrier, for generating pressure pulses in said propagation medium, said pressure pulses converging at a common acoustic focus; and means for energizing said coil means for respectively rapidly displacing said membrane means in said annular zones relative to said acoustic propagation medium in variable chronological relationship for selectively adjusting the position of said acoustic focus of said pressure pulses relative to said geometrical focus.

33. An electromagnetic pressure pulse source comprising:

a housing containing an acoustic propagation medium;

a planar carrier disposed in said housing;

electrically conductive membrane means disposed for interacting with said propagation medium and coil means, forming in combination an annular array having a plurality of planar annular zones disposed on said planar carrier, for generating pressure pulses in said propagation medium;

focusing means disposed in the propagation path of said pressure pulses in said propagation medium for focusing said pressure pulses onto a geometrical focus; and means for energizing said coil means for respectively rapidly displacing said membrane means in said annular zones relative to said acoustic propagation medium in variable chronological relationship for causing said pressure pulses to substantially coincide at a common acoustic focus having a position which is selectively adjustable relative to said geometric focus.

34. An electromagnetic pressure pulse source comprising:

a housing containing an acoustic propagation medium;

a cylindrical electrically conductive membrane means disposed for interacting with said propagation medium and cylindrical coil means, forming in combination an annular array having a plurality of annular zones, for radially emitting pressure pulses in said propagation medium;

an acoustically reflecting surface surrounding said membrane means and said coil means for reflecting said radially emitted propagation pulses onto a geometrical focus; and means for energizing said coil means for respectively rapidly displacing said membrane means in said annular zones relative to said acoustic propagation medium in variable chronological relationship for causing said pressure pulses to substantially converge at a focus having a position which is selectively adjustable relative to said geometrical common acoustic focus.

* * * * *